United States Patent [19]

Berke

[11] Patent Number: 4,851,337

[45] Date of Patent: Jul. 25, 1989

[54] EXTRACTION OF TEST SUBSTANCES

[75] Inventor: Carl M. Berke, Cambridge, Mass.

[73] Assignee: Hygeia Sciences, Inc., Newton, Mass.

[21] Appl. No.: 894,566

[22] Filed: Aug. 8, 1986

Related U.S. Application Data

[63] Continuation-in-part of Ser. No. 817,202, Jan. 8, 1986, abandoned.

[51] Int. Cl.⁴ .......................... C12Q 1/02; C12Q 1/14; C12N 1/06
[52] U.S. Cl. .......................................... 435/29; 435/4; 435/36; 435/259; 435/810; 435/820; 435/885
[58] Field of Search .................... 435/29, 36, 39, 259, 435/820, 885; 427/2, 230, 231

[56] References Cited

U.S. PATENT DOCUMENTS

| | | | |
|---|---|---|---|
| 3,804,663 | 4/1974 | Clark | 427/231 |
| 4,357,142 | 11/1982 | Schall, Jr. et al. | 427/2 |
| 4,363,634 | 12/1982 | Schall, Jr. | 427/2 |
| 4,529,614 | 7/1985 | Barns | 427/2 |
| 4,673,639 | 6/1987 | Slifkin | 435/36 |

FOREIGN PATENT DOCUMENTS 153477 9/1985 European Pat. Off. .

OTHER PUBLICATIONS

Kholy et al., (1974), Applied Microbiology 28(5):836–839.
Hafez et al., (1981), J. Clin. Microbiol. 14(5):530–533.

Primary Examiner—Robert J. Warden
Assistant Examiner—Janelle Graeter

[57] ABSTRACT

A vessel containing a polymeric acid is used in a method and test kit for extracting a bacterial (e.g., streptococcal) antigen from a test sample, for example, preliminary to an immunoassay. To extract the antigen from bacteria in the sample, a precursor reagent is applied to the vessel acid and incubated with the sample. The kit includes a vial containing the acid and another vial containing the precursor. The kit is produced by including the acid polymer in the vial or vessel, e.g., as a pellet or coating.

23 Claims, 1 Drawing Sheet

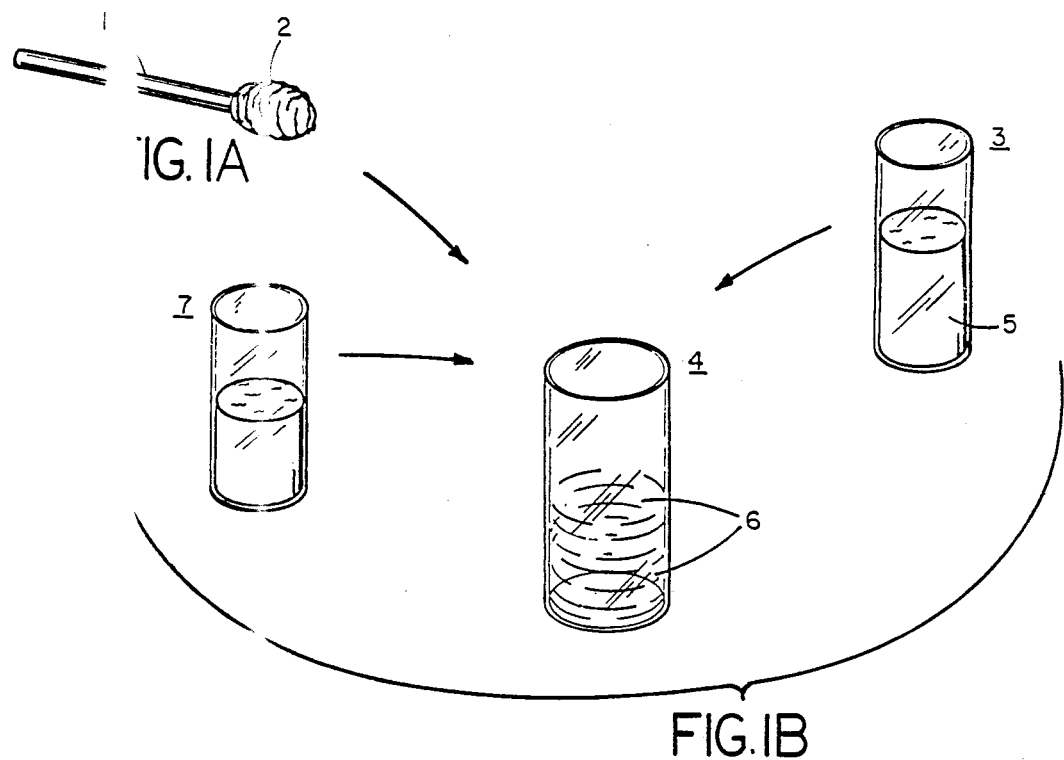

EXTRACTION OF TEST SUBSTANCES

CROSS-REFERENCE TO RELATED APPLICATION

This application is a continuation-in-part of my earlier, co-pending application U.S. Ser. No. 817,202 now abandoned, filed Jan. 8, 1986, which is hereby incorporated by reference.

BACKGROUND OF THE INVENTION

This invention relates to the extraction of bacterial antigens, particularly for immunoassays.

Bacterial antigens are bacterial substances which generate, or which immunospecifically react with, anti-bacterial antibodies. The presence of such an antigen in a sample is standardly detected by an immunospecific reaction with anti-bacterial antibodies.

Some bacterial antigens may be encrypted in larger cell structures which interfere with the immunospecific reaction or with its detection. Moreover, the sample may include other substances such as cell debris, mucus or other flora, which also can infere with the immunospecific reaction or with its detection.

Thus, it is important, e.g., preliminary to an immunoassay, to extract a bacterial antigen from cell structures and other sample components that surround it. This process is known as extracting the bacterial antigen.

Rosenstein, Published European Patent Application 153477, discloses a diagnostic test for group A streptococci in which an enzymatic extraction reagent releases strep A antigen from a swab, and agglutination with antibody immobilized on latex beads is detected.

A more customary rapid extractive medium is a combined solution of acetic acid and sodium nitrite. For example, Kholy et al. (1974) Applied Microbiology 28(5):836–839 and Hafez et al. (1981) J. Clin. Microbiol. 14(5):530–533 disclose a method of extracting protein antigens from streptococci in which $NaNO_2$ and glacial acetic acid are added to a cell preparation. The extracted antigens are then subjected to immunoassay.

Unfortunately, the above-described nitrous acid extraction solution is highly unstable. It is apparent that the acetic acid must be kept separate from the nitrite until just before extraction takes place. Otherwise the instability of the resulting nitrous acid solution can defeat the extraction. Thus if the extractive materials are mixed prematurely there is a decay and the resultant solution becomes unsatisfactory after but a short delay interval.

In addition, the required separate packaging and mixing of the precursors is prone to leakage, inconvenient, time consuming, and liable to error.

Once the extraction is completed, the extractive medium may be neutralized, e.g., with NaOH as disclosed in Kholy et al. or Hafez et al. cited above, and the assay proceeds in conventional fashion.

Accordingly, it is an object of the invention to facilitate the extraction of test substances, as well as the assay of test materials. A related object is to facilitate immunoassays, particularly enzyme immunoassays.

Another object of the invention is to facilitate the extraction of nitrogenous substances, such as streptococcal cell walls. A related object is to completely eliminate the need for separate packaging of liquid acid or precursor prior to extraction.

Still another object of the invention is to reduce the amount of handling required for the extraction of antigens before performing enzymatic assays.

Yet another object of the invention is to eliminate the need for combining sodium nitrite with a liquid activator such as acetic acid. A related object is to eliminate any adverse consequences from the premature combination of an extractive agent with a liquid activator.

SUMMARY OF THE INVENTION

In accomplishing the foregoing and related objects the invention provides for extraction of a bacterial antigen, by transferring a sample which may contain the antigen to the interior of a vessel containing a polymeric acid. A precursor reagent is also transferred to the vessel, and the sample is incubated for a sufficient time to permit the acid to react with the precursor and produce the desired extraction.

In accordance with one embodiment of the invention, the polymeric acid reacts with the precursor to produce a diazotizing medium. For example, the precursor is a nitrite salt, such as sodium or potassium nitrite.

Preferably the bacterial antigen is an antigenic carbohydrate, especially a streptococcal antigen. Preferably the polymeric acid is: a polymeric acid or an anhydride thereof; a polysulfonic acid such as polystyrene sulfonic acid or polyacrylamidosulfonic acid; or a polyphosphoric acid. Specifically preferred polymeric acids are polyacrylic acids such as polymethacrylic acid.

A test kit in accordance with the invention includes a first vial with a polymeric acid and a second vial that includes an extractive precursor. The polymeric acid may be a pellet within the first vial, or it may be a coating on an interior wall of the first vial. Components that may be included with the polymeric acid include a surfactant to assure wetting of the interior wall surfaces, a plasticizer to avoid brittleness, and a fluorescent compound to test for presence and distribution of the acid. In addition, the first vial is an open or stoppered tube, advantageously of plastic. The second vial desirably includes sodium nitrite solution. The activator coating reacts with a sodium nitrite solution to produce an extractive medium for the bacterial antigen. Preferably the polymeric acid in the kit is one of the acids described above.

In a method of producing a structure for the extraction of a test antigen, a vessel is provided and an acidic polymer is included within the vessel. The acidic polymer may be a thin coating or it may be applied to the interior of the vessel as a pellet.

The acidic acid polymer coating may be created by applying the coating applied to the interior of the vessel as a coating solution, and the vessel is continuously rotated to deposit a symmetrical coating on the interior of the vessel as the solvent is evaporated. If a fluorescent tracer is included with the acid, the method of producing may include illuminating the acid in the vial to verify its presence and distribution.

DESCRIPTION OF THE DRAWING

Other aspects of the invention will become apparent after considering several illustrative embodiments taken in conjunction with FIGS. 1A and 1B, which illustrate an extractive procedure in accordance with the invention.

DETAILED DESCRIPTION I. The Process of Extraction

FIG. 1A and FIG. 1B show a test arrangement for the extraction of a bacterial antigen from a substance in a test swab 1 (or a first vial not shown). The swab 1 carries a test substance 2, which also may include a bacterial antigen, such as strep antigen.

In order to conduct an assay for the strep antigen, it is preliminarily necessary to expose the antigen from the test substance 2. For that purpose first and second vials 3 and 4, respectively, are provided. The first vial 3 contains a precursor reagent of sodium nitrite solution 5. The second vial 4 of the extractive test assemblage contains a polymeric acid, e.g., polyacrylic acid coating 6.

To accomplish the extraction the sodium nitrite solution 5 from the first vial 3 is poured into the second vial 4 as indicated by an arrow. The test substance 2 from the swab 1 is inserted or poured into the second vial 4 as indicated by another arrow. This may take place simultaneously, following or preceding the entry of the sodium nitrite into the second vial 4.

The extractive procedure in accordance with FIG. 1A and FIG. 1B contrasts with the typical antigen extraction procedure for streptococcus samples in accordance with the prior art where the reagents are sodium nitrite solution and dilute acetic acid. The instability of the acetic acid-nitrous acid combination has forced users to form the final reagent immediately prior to use. The standard commercial practice is to have the user dispense acetic acid solution and sodium nitrite solution from individual vials for mixing in the extraction vial or tube 4.

By contrast with the prior art, FIG. 1A, and FIG. 1B depict a precoating of the extraction tube 4 with a dry film 6 of polymeric acid. This allows the acetic acid vial to be completely eliminated from the extraction kit, along with the accompanying manual operation. This simplifies not only the final configuration of the assay kit but also the assay protocol, without compromising assay performance.

One suitable polymer is polyacrylic acid MW 5000 (Goodrite 732 from the B. F. Goodrich Company). This polymer forms a clear, colorless, continuous film upon evaporation of its carrier solvent, which can be water. Another suitable polymer is poly(2-acrylamido-2-methyl-1-propane sulfonic acid (available from Aldrich Chemical Co., Milwaukee, Wis.).

In order to promote a uniform coating of the polymer or the interior of the tube 4, an aliquot of a polymer coating solution is dispensed to the bottom of the receiving tube 4. When the tube is hydrophobic, a surfactant is included to assure wetability and uniform coverage. The tube 4 is then rotated continuously in a 70° C. drying oven so that the loading material deposits and concentrates symmetrically along the inner wall of the tube 4, which is desirably inclined during this process to restrict the coating to the bottom of the tube. This ensures that a small volume of sodium nitrite solution will be able to dissolve the entire amount of polyacrylic acid as rapidly as possible and yield the final concentration levels that are needed for the extraction.

Although a thin-film coating is desirable, it is not required. The assay protocol prescribes mechanical agitation of the test specimen. Because the total quantity of polymer for one assay is so small, this provides enough mixing to dissolve even a concentrated pellet of acid polymer. In an alternative fabrication procedure, the coating material is introduced as a dry pellet, or it is introduced in a solvent, at the bottom of the tube, and there is no need for special orientation of the tube during the drying stage.

Trials have been conducted using polystyrene plastic, as well as borosilicate and pyrex glass tubes. When plastic tubes are used, it is desirable to use a surfactant in the coating solution in order to ensure wetting.

To avoid brittleness and chipping of the coating, an inert non-volatile hydrophilic plasticizer such as ethylene glycol can be included in the coating formulation. Preferably the plasticizer constitutes 10–80% (most preferably about 25%) of the final dry coating by weight.

A fluorescent tracer, such as a stilbene derivative, also can be added to the coating, so that coating presence or coating integrity can be verified easily and non-destructively using an ultraviolet inspection lamp.

After the antigens are extracted in accordance with FIG. 1A and FIG. 1B, the reagent is neutralized, for example by a solution from a vial 7 as shown by an additional arrow. An assay can be performed with any of a wide variety of test kits, as described below.

Polymeric acid coating and extraction of bacterial antigen will now be illustrated with specific examples, which are offered as illustrative and not as limitations.

EXAMPLE 1

Polyacrylic Acid Coating

To prepare an acid tube-coating solution, 50microliters of 50% polyacrylic acid MW 5000 were diluted with 0.50 mL (milliliters) of water. 0.50 mL of Tween 20 surfactant (from Sigma Chemical Company of St. Louis, Mo. were then diluted with 500 mL of water. 0.20 mL of the resulting mixture were combined with the diluted polyacrylic acid by vortex mixing. 50 microliters of this coating solution were next dispensed directly to the bottom of a three mL, conical polystyrene tube (Sarstedt Model No. 73.646 of Princeton, N.J.). The tubes were then coaxially attached to a motorized rotator and placed in a 70° F. convection oven at an incline of 20° for three hours until thoroughly dry.

EXAMPLE 2

Polyacrylic Acid Coating with Plasticizer

In order to avoid brittleness and increase coating adherence, a non-volatile hydrophilic plasticizer was added to the coating solution. For example 8.4 g Goodrite 732 polyacrylic acid (B. F. Goodrich, Cleveland, OH), 50% w/w solution (Mw 5,100), was combined with 11 mL $H_2O$, 0.30 mL Tween 20 (Sigma Chemical Co., St. Louis, MO), 1.05 mL Carbowax 350 (Union Carbide, Danbury, CT), and 0.1 mL Intrawhite diluted 1:100 (Crompton & Knowles, Rumford, RI). The coating was applied to a vial as described in Example 1.

EXAMPLE 3

Polyacrylamidosulfonic Acid Coating (P-AMPS)

A pAMPS coating was prepared by combining and thoroughly mixing 10 g poly (2-acrylamido-2-methyl-1-propane sulfonic acid), available as 10% w/w aqueous solution from Aldrich Chemical Co., Milwaukee, Wis., with 10 mL $H_2O$ and 0.3 mL Tween 20. The coating was applied to a vial as described in Example 1.

EXAMPLE 4

Polystyrene Sulfonic Acid Coating

A polymeric acid coating was prepared by mixing 5 g Versa TL 72 (20% w/w polystyrene sulfonic acid sold by National Starch co., Bridgewater, N.J.) with 11.4 mL water and 0.30 g Tween 20. 50 microliters of this solution was dispensed to 12×55 polystyrene test tubes then dried at 70° C. for 3 hours.

EXAMPLE 5

Bacteria Extraction Using Polyacrylic Coating

Acid coated vials prepared in accordance with Example 1 were used in an assay for Group A streptococcus. The extraction performance for the acid coated vials was compared with that for the conventional generation of nitrous acid and tested in an enzyme immunoassay.

Positive sample swabs were seeded with a solution of $10^6$ organisms per milliliter of strep A in a Phosphate Buffered Saline (PBS) solution. Extraction tubes were used in accordance with Table 1 below. Tubes of Type A were prepared as noted above for Example 1 and tubes of Type B are the same tube without an acid coating and served as a control.

TABLE 1

| ADDED REAGENTS | EXTRACTION REAGENT FORMULAE | |
|---|---|---|
|  | TUBES OF TYPE A | TUBES OF TYPE B |
| Sodium Nitrite | 0.30 mL at 2.7 Molar | 0.20 mL at 4 Molar |
| Acetic Acid | None | 0.10 mL at 1.5 Molar |

Swabs were incubated in the individual tubes for 3 minutes and 0.30 mL of neutralization buffer added to each.

The neutralization buffer was one molar N-hydroxyethyl-piperazine-N'-ethanesulphonic acid (available from Research Organics Inc., Cincinnati, Ohio), adjusted to pH 8 with 0.25% w/w bovine serum albumin and 0.2% w/w Tween 20.

EXAMPLES 6-8

Bacterial Extraction with Other Polymeric Acids

Tubes containing polymeric acid as described in each of Examples 2-4 were subjected to test swabs generally using the procedure of Example 5. After extraction, the extract was neutralized.

II. Assaying The Extract

The extracts prepared according to the invention are useful in immunoassays which are generally well-known. For example, the extract can be assayed with sandwich ELISA system utilizing an anti-strep antibody-coated dipstick. Specifically, one antibody is immobilized to a polystyrene paddle, and a second enzyme-labelled antibody is added to the solution to be assayed.

The following examples illustrate one use for antigen extracted by the technique of part I, above.

EXAMPLE 9

Sandwich ELISA Paddle Assay

In one example of the sandwich ELISA paddle assay described, 0.45 mL of extract from Example 5 was mixed with 0.050 mL of antibody conjugate (having a horseradish peroxidase label, in the molar ratio of 1:1.5 antibody to label). The assay can then be performed with a polystyrene paddle coated with rabbit anti-strep immunoglobulin. The resultant immunocomplex on the paddle, Ab-Ag-AbE, is formed by incubation of the paddles in the extract/conjugate mixture for 20 minutes, followed by removal and washing for 3 seconds under running tap water. The paddle was subsequently incubated for 10 minutes in chromogen solution which was previously prepared by combining 3 parts of tetramethylbenzidine solution (1.5 grams per liter in methanol) with 7 parts citrate-phosphate buffer (0.05 molar at pH 5.0) containing 0.007% hydrogen peroxide.

The results obtained using the above-described ELISA paddle method are summarized in Table 2. Units are in optical density at a wavelength of 630 nanometers.

TABLE 2

| Tube Type | Swabs | | | |
|---|---|---|---|---|
|  | Pos. No. 1 | Pos. No. 2 | Neg. No. 1 | Neg. No. 2 |
| A (with dry acid) | 0.763 | 0.796 | 0.021 | 0.021 |
| B (with liquid acid) | 0.595 | 0.769 | 0.015 | 0.025 |

As noted above, the results are in optical density units at 630 nanometers. At the indicated wavelength, an optical density greater than 0.05 indicates a positive result. It is to be noted that the invention gives uniform results of equal sensitivity or greater than does the standard extraction of the prior art.

EXAMPLES 10-12

Extraction and Assay Using Vials Prepared as in Examples 6-8

The extracts prepared in Examples 6-8 were assayed with a paddle assay generally using the procedure in Example 9.

An alternative to the paddle assay described in the above examples is a flow-through ELISA assay, in which a first antibody is immobilized on a membrane and the extract is poured through the membrane, the antigen being trapped by the first antibody. To detect the antigen, it is reacted (either before or after reaction with the membrane) with a second antibody that is enzyme labeled. Depending on the enzyme labeling system used, the membrane-immobilized antibody may also be co-immobilized with an enzyme, so that the two enzymes catalyze separate reactions which together generate color from a suitable substrate and chromogen.

Other aspects of the invention will be apparent to those of ordinary skill in the art.

I claim:

1. A method of extracting a bacterial antigen from a test sample which comprises the steps of:
    (a) reacting in a vessel a precursor reagent with a solid polymeric acid, or with a solid polycarboxylic acid anhydride capable of forming a polymeric acid, to form an extractive mixture, said pecursor reagent being capable of forming nitrous acid when reacted with said polymeric acid; and
    (b) incubating said sample with said extractive mixture to extract said antigen.
2. The method of claim 1 wherein said bacterial antigen comprises an antigenic carbohydrate.
3. The method of claim 1 wherein said bacterial antigen is a streptococcal antigen.

4. The method of claim 1 wherein said precursor reagent comprises a nitrite salt.

5. The method of claim 4 wherein said salt is sodium nitrite.

6. The method of claim 1 wherein said solid polymeric acid is a polycarboxylic acid.

7. The method of claim 1 wherein said solid polymeric acid is polysulfonic acid.

8. The method of claim 7 wherein said polysulfonic acid is polystyrene sulfonic acid.

9. The method of claim 1 wherein said solid polymeric acid is a polyphosphoric acid.

10. The method of claim 1 wherein said solid polymeric acid is a polyacrylic acid.

11. The method of claim 1 wherein said extractive mixture is formed by an acid consisting essentially of a polymethacrylic acid.

12. The method of claim 1 in which said polymeric acid or said polycarboxylic acid anhydride is provided in a test container, and said precursor reagent is added to said test container to form said extractive mixture.

13. A test kit comprising:
a first vial including a solid polymeric acid or a solid polycarboxylic acid anhydride capable of forming a polymeric acid and
a second vial including an extractive precursor reagent, said extractive precursor reagent being capable of forming nitrous acid when reacted with said polymeric acid.

14. A test kit as defined in claim 13 wherein said solid polymeric acid is a coating on an interior wall of said first vial.

15. A test kit as defined in claim 14 wherein said solid polymeric acid comprises a fluorescent compound.

16. A test kit as defined in claim 13 wherein said extractive precursor reagent comprises a nitrite salt.

17. A test kit as defined in claim 16 wherein said nitrite salt is sodium nitrite.

18. A test kit as defined in claim 13 wherein said solid polymeric acid is a polycarboxylic acid.

19. A test kit as defined in claim 13 wherein said solid polymeric acid is polysulfonic acid.

20. A test kit as defined in claim 19 wherein said polysulfonic acid is polystyrene sulfonic acid.

21. A test kit as defined in claim 13 wherein said solid polymeric acid is a polyphosphoric acid.

22. A test kit as defined in claim 13 wherein said solid polymeric acid is a polyacrylic acid.

23. A test kit as defined in claim 13 wherein said solid polymeric acid consists essentially of a polymethacrylic acid.

* * * * *

UNITED STATES PATENT AND TRADEMARK OFFICE
CERTIFICATE OF CORRECTION

PATENT NO. : 4,851,337
DATED : July 25, 1989
INVENTOR(S) : Carl M. Berke

It is certified that error appears in the above-identified patent and that said Letters Patent is hereby corrected as shown below:

On the title page;

U.S. Patent Documents, 4,529,614, "Barns" should be --Burns--.

Column 3, lines 1-2, "I. The Process of Extraction" should be a new heading on a separate line.

Column 3, line 35, delete "," after "1A".

Column 4, lines 33-34, "50microliters" should be -- 50 microliters--.

Column 4, line 37, insert --)-- after "Mo.".

Column 4, lines 51-52, "Goo-drite" should be --Good-rite--.

Column 4, line 61, "(P-AMPS)" should be --(p-AMPS)--.

Signed and Sealed this

Third Day of April, 1990

Attest:

HARRY F. MANBECK, JR.

Attesting Officer

Commissioner of Patents and Trademarks